United States Patent
Niedermeier

(10) Patent No.: US 10,262,405 B2
(45) Date of Patent: Apr. 16, 2019

(54) OPTICAL INSPECTION METHOD AND OPTICAL INSPECTION DEVICE FOR CONTAINERS

(71) Applicant: KRONES AG, Neutraubling (DE)

(72) Inventor: Anton Niedermeier, Offenstetten (DE)

(73) Assignee: KRONES AG, Neutraubling (DE)

( * ) Notice: Subject to any disclaimer, the term of this patent is extended or adjusted under 35 U.S.C. 154(b) by 62 days.

(21) Appl. No.: 15/320,214

(22) PCT Filed: Jun. 26, 2015

(86) PCT No.: PCT/EP2015/064521
§ 371 (c)(1),
(2) Date: Dec. 19, 2016

(87) PCT Pub. No.: WO2016/023668
PCT Pub. Date: Feb. 18, 2016

(65) Prior Publication Data
US 2017/0154417 A1 Jun. 1, 2017

(30) Foreign Application Priority Data

Aug. 14, 2014 (DE) .................. 10 2014 216 188

(51) Int. Cl.
*H04N 7/18* (2006.01)
*G06T 7/00* (2017.01)
(Continued)

(52) U.S. Cl.
CPC ............ *G06T 7/0004* (2013.01); *B07C 5/342* (2013.01); *B07C 5/3408* (2013.01);
(Continued)

(58) Field of Classification Search
CPC .................................................. G01N 21/90
(Continued)

(56) References Cited

U.S. PATENT DOCUMENTS 4,213,702 A * 7/1980 Bryant ............... G01N 21/9054
250/223 B
4,376,951 A    3/1983 Miyazawa
(Continued)

FOREIGN PATENT DOCUMENTS

DE        10140009 A1    3/2003
DE     102007009769 A1   8/2008
(Continued)

OTHER PUBLICATIONS

Hui-Min Ma et al.: "A Glass Bottle Defect Detection System without Touching", Machine Learning and Cybernetics, 2002 International Conference on Nov. 4-5, pp. 628-632.
(Continued)

*Primary Examiner* — Anand S Rao
(74) *Attorney, Agent, or Firm* — Marshall, Gerstein & Borun LLP

(57) ABSTRACT

An optical inspection method for containers. A container is at least partly illuminated or transilluminated with light of an illuminating device and captured from different viewing directions (R4-R6) as a camera image in each case by at least one camera. In a first image analysis step, first image information of a first inspection zone (A) of the container, for example a stain on a container front face, is ascertained from at least two of the camera images by stereoscopically pairing image points. In a second image analysis step, an individual camera image of the two camera images is analyzed, wherein the first image information is first excluded and second image information of a second inspection zone (B) of the container, for example a crack of a container rear face, is then ascertained.

11 Claims, 2 Drawing Sheets

Figure 1:
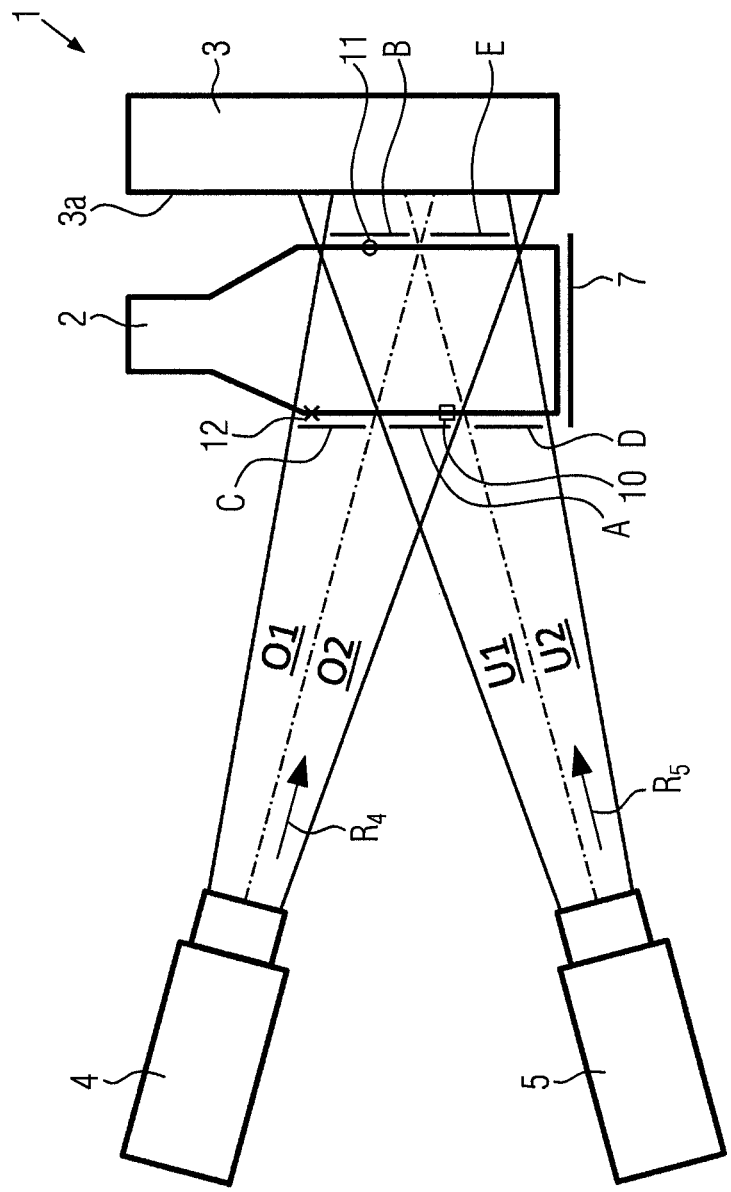

(51) Int. Cl.
    *B07C 5/34*               (2006.01)
    *B07C 5/342*           (2006.01)
    *G01N 21/88*           (2006.01)
    *G01N 21/90*           (2006.01)
    *H04N 13/254*         (2018.01)
    *H04N 13/243*         (2018.01)

(52) U.S. Cl.
    CPC ..... *G01N 21/8851* (2013.01); *G01N 21/9018* (2013.01); *G01N 21/9036* (2013.01); *H04N 13/243* (2018.05); *H04N 13/254* (2018.05); *G01N 2021/8861* (2013.01); *G01N 2021/8864* (2013.01); *G01N 2201/12* (2013.01); *G06T 2207/10012* (2013.01)

(58) Field of Classification Search
    USPC ...................................... 348/86–95, 125–134
    See application file for complete search history.

(56) References Cited

U.S. PATENT DOCUMENTS

| | | | | |
|---|---|---|---|---|
| 4,500,203 A | * | 2/1985 | Bieringer | G01N 21/9036 209/525 |
| 4,586,080 A | * | 4/1986 | Hoyt | B07C 5/3422 348/133 |
| 5,729,340 A | * | 3/1998 | Griesbeck | B07C 5/122 250/223 B |
| 6,031,221 A | * | 2/2000 | Furnas | G01N 21/9036 209/524 |
| 6,584,805 B1 | * | 7/2003 | Burns | C03B 9/41 209/524 |
| 2014/0311256 A1 | * | 10/2014 | Cochran | G01L 5/24 73/862.08 |

FOREIGN PATENT DOCUMENTS

| | | |
|---|---|---|
| DE | 102008025658 A1 | 12/2009 |
| DE | 102008063076 B3 | 4/2010 |
| DE | 102009011270 A1 | 9/2010 |
| DE | 102009039612 A1 | 3/2011 |
| DE | 102011004584 A1 | 8/2012 |
| DE | 102011083377 A1 | 3/2013 |
| DE | 102012022474 A1 | 5/2014 |
| DE | 102013222827 A1 | 5/2015 |
| EP | 0663069 A1 | 7/1995 |
| EP | 2623962 A1 | 8/2013 |
| FR | 2991052 A1 | 11/2013 |
| JP | 2013134099 A | 7/2013 |
| WO | WO-2006/011803 A2 | 2/2006 |

OTHER PUBLICATIONS

German Search Report for a Application No. 102014216188.6, dated Aug. 28, 2015.

* cited by examiner

OPTICAL INSPECTION METHOD AND OPTICAL INSPECTION DEVICE FOR CONTAINERS

CROSS-REFERENCE TO RELATED APPLICATIONS

The present application is the US national phase of International Patent Application No. PCT/EP2015/064521, filed Jun. 26, 2015, which application claims priority to German Application No. DE 102014216188.6, filed Aug. 14, 2014. The priority application, DE 102014216188.6, is hereby incorporated by reference.

TECHNICAL FIELD

The invention relates to a method and a device for optical inspection of.

PRIOR ART

For example, a transilluminating light inspection method is known from DE 10 2009 011 270 A1 in which the same inspection zone of a container wall is captured with two cameras from two different viewing directions with an overlapping field of view. The two camera images are then equalized during image processing and made to overlap in the overlapping area. In this way, corresponding image information can be separated from interference information.

Furthermore, WO 2006/011803 A2 discloses a method for recognizing foreign objects in containers in which the container is illuminated by a light source and is captured by several cameras from different viewing directions. The three-dimensional position of a foreign body can be reconstructed by way of stereoscopic techniques in that the information from several different camera images is correlated.

A disadvantage of the known methods is that, for inspection of all inspection zones on the container, a correspondingly large number of recordings with overlapping image areas are necessary and the inspection effort is therefore particularly high.

Furthermore, an inspection device for optical inspection of bottles is known from DE 10 2008 063 076 B3 in which the field of view of a camera is subdivided using a mirror cabinet so that the container can be simultaneously captured from several viewing directions.

DISCLOSURE OF THE INVENTION

It is the object of the present invention to provide an optical inspection method for containers which operates more efficiently and is thereby less complex.

Due to the fact that the first image information ascertained previously in the stereoscopic image analysis is excluded during the second image analysis step, the corresponding image points can no longer be misinterpreted in the further analysis. Furthermore, it is due to the stereoscopic pairing in the first image analysis step known that the first image information must be located in the first inspection zone. Consequently, it can also in the second image analysis step be taken into account in the analysis that the remaining image objects must be located outside the first inspection zone. The second image information can thereby be ascertained more reliably without having to capture further overlapping camera images, which makes the method particularly efficient.

The optical inspection method can be performed in a container manufacturing and/or beverage processing system. The optical inspection method can be used after the production of a container, after cleaning a new or recycled container, downstream and/or upstream of a filling system. The container manufacturing system can be, for example, a stretch blow-molding machine for PET bottles. The beverage processing system can comprise a rinser, a filler, a capper, a labeler, and/or a packaging machine. The optical inspection method can be performed with an optical inspection device. The optical inspection method can comprise a transillumination, dark field, and/or reflected light method. Dark field method can there mean that the container is illuminated from a direction of illumination that is oblique relative to the viewing direction of the camera, where the camera does not directly record the light-emitting surface of the illuminating device. As a result, the light is deflected, for example, at defects, in such a manner that it passes into the camera. Consequently, the defects appear lighter in the camera image than the surroundings.

The illuminating device can comprise a light source and/or a scattering body. Preferably, the illuminating device can comprise a large-area light-emitting disk which is larger than the container outline of the container to be inspected in the side view. The light-emitting surface can be a scattered or frosted glass pane. The light source can comprise a fluorescent tube, a light bulb, and/or an LED. The illuminating device can be configured as a transillumination, dark field, and/or reflected light illuminating device. Dark-field illuminating device can there mean that the device emits light axially relative to the container axis onto the container mouth and/or the container base, and the container is inspected at least partly with the viewing direction being perpendicular to the container axis.

The containers can be provided to receive beverages, hygiene products, pastes, chemical, biological and/or pharmaceutical products. The containers can, in particular, be plastic bottles, glass bottles, cans, and/or tubes. The plastic containers can be, in particular, PET, HD-PE or PP containers or bottles. They can also be containers made of biodegradable material. The containers can be empty or filled partially or entirely with a product.

That "a container is at least party illuminated and/or transilluminated with light of an illuminating device" can presently mean that only a partial region of the container is inspected with the optical inspection method. This can be the container mouth, the side wall, and/or the base of the container. "Transilluminating" can presently mean that the container is transilluminated in transilluminating light or in the dark field. However, transillumination can also mean that the container is transparent, translucent with respect to the spectral wavelength(s), and a different kind of illumination, for example, dark field illumination, is employed.

The camera can be a CMOS or a CCD camera. A lens on the camera can be intended to image the container onto an image sensor of the camera. The camera can via a data interface be connected to a machine controller and/or an image processing device. The perspective via the lens can have an entocentric, telecentric or entocentric behavior.

The image processing device can comprise a microprocessor, a memory, a display unit, an input keyboard, a pointing instrument and/or a data interface. The image processing device can be configured to analyze camera images with image processing algorithms.

"A container is at least partly [ . . . ] captured from different viewing directions as a camera image in each case by means of at least one camera" can presently mean that the container (or a partial region thereof) is captured from different viewing directions in each case with a separate camera. A mirror cabinet can also be arranged in front of the camera for capturing the different viewing directions. In this regard, each of the camera images can be associated with a viewing direction of the mirror cabinet. In other words, in this case, the overall image captured with the mirror cabinet and a camera is divided into several camera images, each of which is associated with a viewing direction.

An inspection zone can correspond to a three-dimensional domain or a section of the container. For example, an inspection zone can correspond to the entire or a portion of the container side wall. It is also conceivable that an inspection zone corresponds to the container mouth or the container base. The individual inspection zones can not overlap each other. An inspection zone can be subdivided into several units. In order to not have the interested image information be destroyed by the division into a sufficient size by subdivision, a respective overlap of the subdivisions can be provided.

The image information can comprise features of the container, a stain, at least one portion of a label, material embossment, a container defect, such as a crack, a container identifier and/or a print. The image information can in particular comprise the position, the size, and/or the type of the feature on the container. In other words, the image information can comprise any suitable information characterizing the container, its content, and/or a stain on the container. Furthermore, the image information can contain information about the fact that no stain on the container has been ascertained in the camera image. The image information can be extractable from the camera images by use of image processing algorithms. For example, the image processing algorithms can comprise filters such as, for example, a threshold, edge, and/or contrast filter.

Stereoscopic pairing can comprise two-dimensional superpositioning of the two camera images and optionally perspective equalization. Stereoscopic pairing can presently also mean that 3D points on the container are associated with the respective image points of the two cameras. With the stereoscopic pairing, the three-dimensional position of the feature on the container can be ascertained. Stereoscopic pairing can comprise a photogrammetric analysis or a triangulation algorithm, respectively. The image points can comprise pixels, image sections or the like in the two camera images.

That "in a second image analysis step, an individual camera image of the two camera images is analyzed" can presently mean that exactly one of the two camera images used in the stereoscopic pairing is analyzed without there taking into account the other camera image beyond the already ascertained first image information. In the second image analysis step, algorithms or image evaluation methods, respectively, can be used which process only gray and/or color values of the camera image and/or the pixel positions.

"The first image information is excluded" can presently mean that the first image information is in the camera image deleted, marked or otherwise suitably disregarded in the second image analysis step.

It is presently conceivable that the first inspection zone of the container is associated with the container front face (in the viewing direction of the camera) and the first image information is there first ascertained by stereoscopic pairing and then the second inspection zone is associated with the container rear face which is in the viewing direction disposed therebehind. The first image information disposed thereinfront can now first be deleted from the camera image prior to the analysis of the second image information disposed therebehind. Consequently, also image information which is initially covered by the first image information disposed thereinfront can therefore also be ascertained.

In the optical inspection method for containers, one of the camera images can be analyzed in a third image analysis step, where the second image information is first excluded and then third image information of a third inspection zone of the container is ascertained. By iterative exclusion of the first and second image information, it is possible to reliably inspect a container section which is captured only by one camera image, where in particular image information is excluded which lies behind the third inspection zone and is nevertheless captured due to the transparency of the container. The camera image analyzed in the third image analysis step can be any camera images captured by the camera.

That "the second image information is excluded" can presently mean that the second image information is in the camera image deleted, marked or otherwise suitably disregarded in the third image analysis step.

The first, the second, and/or the third image analysis step can be carried out one after the other according to their numbering.

The second inspection zone can in the viewing direction of the camera image used in the second image analysis step be arranged behind the first inspection zone, and the third inspection zone can in the viewing direction of the camera image used in the third image analysis step be arranged in front of the second inspection zone. As illustrated above, image information which is located behind the third inspection zone and can therefore distort the inspection result can thus be excluded particularly well.

In the third image analysis step, a different camera image can be analyzed than in the second image analysis step. For example, two camera images can first be analyzed by stereoscopic pairing and the ascertainment of further image information in a further camera image of a third viewing direction can be improved.

The third inspection zone can only be captured by the camera image analyzed in the third image analysis step. As described above, it is thereby possible to more reliably inspect a container section which is captured only by one camera image.

The image information can be ascertained by an imaging rule of the camera which correlates spatial points and image points with one another. Such an imaging rule can image a 3D point by way of a central projection through a pupil of the camera lens onto an image point of the camera sensor, where the location and the size of the camera sensor and lens parameters can with the central projection be taken into account. The lens parameters can comprise a focal length, a pupil position, a focal distance and/or parameters for lens aberration. In other words, the imaging rule comprises an equation with which a 3D point is imaged in the field of view of the camera onto a corresponding image point of the camera image.

The inspection zones can each be associated with different sections of the container. By associating the inspection zones and having knowledge of the container geometry, the efficiency and reliability of the optical inspection method can be further increased by way of plausibility checks.

In addition, the invention with claim 9 provides an optical inspection device for containers, with an illuminating device and at least one camera which is optionally at least party directed onto a light-emitting surface of the illuminating device, and with an image processing device, characterized in that the image processing device is configured to perform the optical inspection method according to at least one of the claims 1-8.

It is therewith possible to perform the optical inspection method described above in the optical inspection device, and therewith analyze the camera images more efficiently and reliably as illustrated in detail above.

The image processing device can comprise a microprocessor, a memory, a display unit, an input keyboard, a pointing instrument and/or a data interface, for example, to the camera. The image processing device can be disposed in the camera or externally in a machine control or a computer, respectively. The image processing device can be a computer or a machine controller.

The optical inspection device can be arranged in a container manufacturing and/or beverage processing system. The inspection device can be disposed upstream or downstream of a filling assembly for filling a product into the containers. The inspection device can also be disposed downstream of a stretch blow-molding machine for PET bottles. The inspection device can be disposed between a stretch blow-molding machine and a filling machine.

The inspection device can also be disposed in a system for recycling containers.

A mirror cabinet can be arranged in front of the camera to capture several viewing directions onto a container in one camera image. The mirror cabinet can be configured to respectively capture two or more viewing directions in one overall image of the camera as a camera image. A camera images can there be associated with one viewing direction of the mirror cabinet. The mirror cabinet can be configured to capture precisely three viewing directions onto a container with one camera image.

Furthermore, the optical inspection device can individually or in any combination also comprise the features previously described with respect to the transilluminating inspection method.

In addition, the invention with claim 11 provides a computer program product on a data carrier comprising machine commands for a microprocessor for performing the optical inspection method according to at least one of the claims 1-8. The machine instructions can comprise commands of a programming language, a meta-language, and/or an assembler language.

The data carrier can be a storage module, a hard disk, a floppy disk, a CD, a DVD, a Blue Ray and/or a USB memory.

Figure 2:
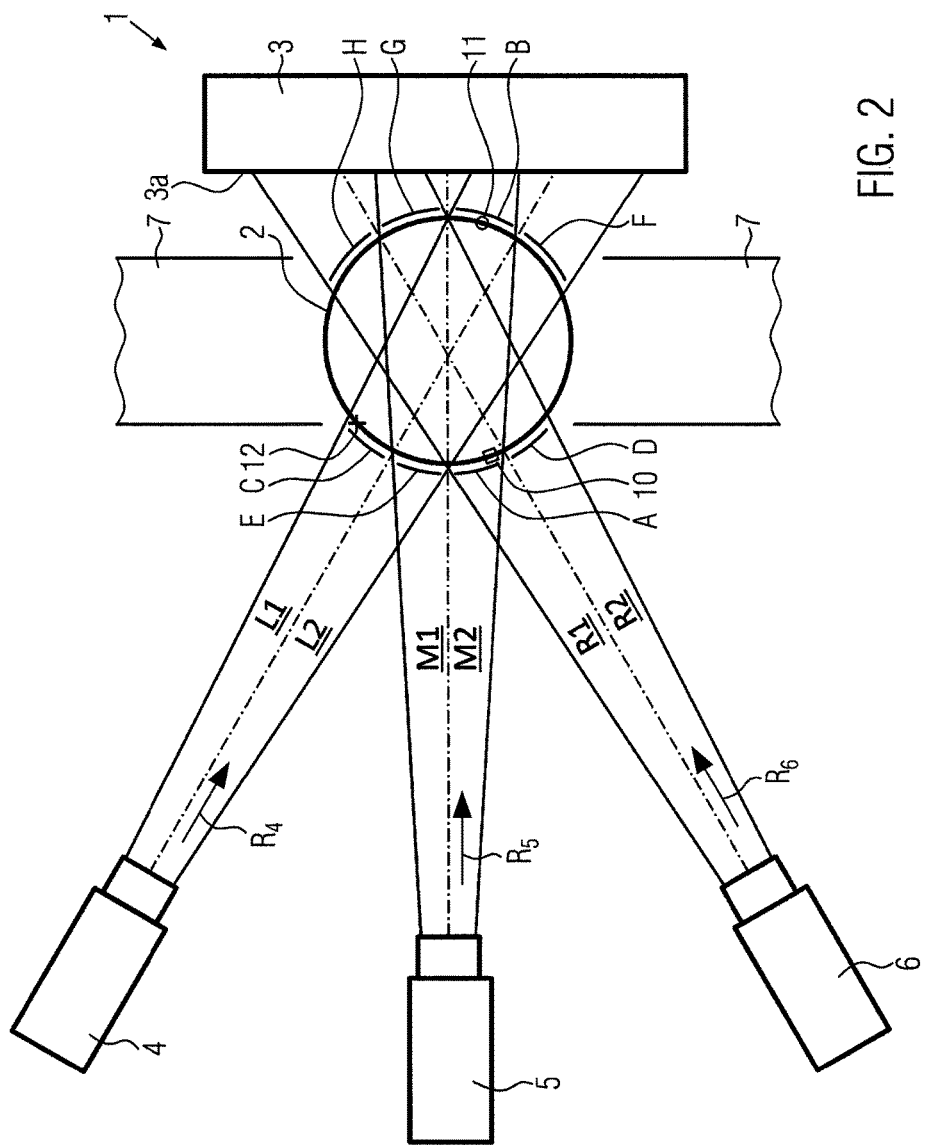

Further features and advantages of the invention shall be explained below with reference to the figures by way of example, where FIG. 1 shows a representation in a lateral view of an embodiment of an optical inspection device for containers when performing the optical inspection method; and FIG. 2 shows a representation in a top view of an embodiment of an optical inspection device for containers when performing the optical inspection method.

FIG. 1 shows a representation in a lateral view of an optical inspection device 1 for containers 2 when performing the optical inspection method. It can be seen that container 2 is transported on a conveyor belt 7 between an illuminating device 3 and two cameras 4 and 5 and is there transilluminated. The direction of transport in FIG. 1 runs perpendicular to the drawing plane. Illuminating device 3 comprises light-emitting surface 3a which emits homogeneously distributed light. It passes through container 2 to cameras 4 and 5 and is there captured as a camera image. However, it is also conceivable that container 2 is alternatively or additionally inspected by way of at least one further illuminating device in incident light and/or the dark field.

It can also be seen that different sections of container 2 are respectively associated with the different inspection zones A-E. Container 2 shown here has a piece of mold 10 in the region of the first inspection zone A, a crack 11 in the region of the second inspection zone B, and a label residue 12 in the region of the third inspection zone C. These objects 10-12 are to be recognized with the optical inspection method described below, and container 2 is then to be sorted out.

It can also be seen that first camera 4 is in the viewing direction $R_4$ directed from obliquely above onto the container side wall. The image field of camera 4 is there roughly divided into parts 01 and 02. Part 01 there captures inspection zones C and B, and part 02 inspection zones A and E. Furthermore, second camera 5 captures container 2 from the viewing direction $R_5$ from obliquely below. Here as well, the image field of the second camera 5 is subdivided into parts U1 and U2, where part U1 captures inspection zones A and B and part U2 inspection zones D and E, respectively. It is understood that this division is purely by way of example in order to explain the embodiment. However, any arbitrary other division of the image fields is conceivable.

The optical inspection method is performed with optical inspection device 1 as follows One camera image is respectively captured with the two cameras 4 and 5 from the two viewing directions $R_4$ and $R_5$. This occurs substantially simultaneously. Container 2 is there transilluminated by the light of light-emitting surface 3a being emitted from illuminating device 3, so that both the rear and the front face of container 2 are visible in the camera images. However, inspection zones C and B, respectively, A and E are superimposed in the camera image of first camera 4. Furthermore, inspection zones A and B, respectively, D and E are superimposed in the camera image of camera 5.

In the first image analysis step, image points of the two camera images are now superimposed by stereoscopic pairing. It would in a telecentric image be possible, for example, to superimpose the image points two-dimensionally directly in the overlapping area. On the other hand, by use of an imaging rule and with knowledge of the lens or camera parameters, the individual camera images can also be equalized and also superimposed two-dimensionally. When superpositioning the two camera images, stain 10 then appears at the expected image points in the region of inspection zone A. If the stain were within the container or on the rear face, then it would appear doubled in the area of overlap of the two camera images and could there be recognized as not belonging to first inspection zone A. Stain 10 is now stored as first image information with the type, the location, and the size in a memory. In other words, stain 10 is respectively visible in both partial image fields 02 and U1 in the lower region.

In the second image analysis step, only the camera image of second camera 5 is now used. Stain 10 as well as crack 11 can there be seen in part U1 of the image field of second camera 5. However, no stain is captured in second part U2. Since stain 10 has already been recognized in the first image analysis step, its first image information is first deleted from the camera image or marked as being recognized, respectively. The camera image is now further analyzed with the known image evaluation algorithms. For example, crack 11 is detected as a blackening by use of a threshold value. As it is further known that container 2 is empty, detected crack 11 can be associated with second inspection zone B. The type, the location, and the size of crack 11 are now stored in the memory as second image information.

It is additionally or alternatively conceivable that the image points of crack 11 in the two camera elements are correlated by stereoscopic pairing by way or an imaging rule of cameras 4, 5 since second inspection zone B is captured both with part 01 of first camera 4 and also with part U1 of second camera 5.

In a third image analysis step, only the camera image of first camera 4 is then analyzed with respect to inspection zone C, which is captured exclusively with part 01. Accordingly, it is not possible to accomplish the inspection of inspection zone C by stereoscopically pairing image points. First, like also in the second image analysis step, the second image information (of crack 11) is excluded from the further analysis. The camera image is subsequently analyzed with image processing algorithms known per se and label residue 12 is recognized as a blackening. Here again, the type, the location, and the size are determined as third image information and stored in a memory.

Overall, the reliability of detecting errors in the area of third inspection zone C is increased by excluding the previously ascertained image information, thereby increasing the efficiency of the inspection method. This makes it possible in the optical inspection method to perform the inspection more reliably in non-overlapping image regions.

FIG. 2 shows a further embodiment in a top view of an optical inspection device 1 for containers 2 when performing the optical inspection method. It can be seen that container 2 is transported with a conveyor belt 7 between an illuminating device 3 and two cameras 4 and 5 and is transilluminated. Light is here as well emitted by illuminating device 3 in the region of light-emitting surface $3^a$, transilluminates container 2 and is captured by cameras 4-6. It is further conceivable that container 2 is alternatively or additionally inspected by way of at least one further illuminating device in incident light and/or the dark field. Optical inspection device 1 shown in FIG. 2 differs from that in FIG. 1 in that three instead of two cameras capture container 2. An even larger area can thereby be inspected circumferentially on container 2.

Accordingly, container 2 is also divided into a total of eight inspection zones A-H. Camera 4 in the viewing direction $R_4$ captures third inspection zone C and second inspection zone B with the first part of the image field L1, and inspection zones E and F with the second part L2, respectively. Furthermore, second camera 5 in the viewing direction $R_5$ captures inspection zone E and G with the first part M1 and with the second part M2 the first inspection zone A and the second inspection zone B. Furthermore, third camera 6 in the viewing direction $R_6$ captures inspection zone A and inspection zone H with the first part R1 and with the second part R2 the inspection zones D and G.

The optical inspection method is in optical inspection device 1 shown in FIG. 2 used as follows:

A camera image of container 2 is first captured by the three cameras 4, 5 and 6 substantially simultaneously from the viewing directions $R_4$-$R_6$ illustrated, where the container is transilluminated with illuminating device 3.

Subsequently, those camera images of the second and third cameras 5, 6 are in a first image analysis step analyzed by stereoscopically pairing image points. This results in an overlap, which has been captured with both camera images, arising in the region of first inspection zone A. With the stereoscopic pairing, stain 10 appears in a right region in both parts M2 and R1. The type, the location, and the size of stain 10 are then stored as first image information in a memory.

In a second image analysis step, the camera image of second camera 5 is now analyzed. It is there already known from the first image information that stain 10 is located there in part M2 and the corresponding image point is therefore excluded from further analysis. Furthermore, a crack 11 is in the same part M2 of the camera image detected on the container rear face in the second inspection zone B. Since the superimposed image information of stain 10 has already been deleted, the crack can be recognized particularly reliably with image processing algorithms. The type, the location, and the size of crack 11 are now stored as second image information in the memory.

In the subsequent third image analysis step, the camera image of camera 4 alone is analyzed. It captures in part L1 both the already known crack 11 as well as additionally a label residue 12 in the third inspection region C. Since the crack 11 is already known from the second image information, it is first removed from the camera image, whereby label residue 12 superimposed therewith becomes easier to recognize. It can also be seen that the third inspection zone C is only captured by first camera 4. Consequently, no stereoscopic pairing is therefore possible in inspection zone C. However, higher recognition reliability is possible in the third image analysis step due to the optical inspection method described, since crack 11 has already been recognized in the camera image and was therefore excluded from further processing.

It is understood that objects can in the region of the inspection zones D-H also be recognized by way of the optical inspection method described with reference to FIGS. 1 and 2. Moreover, optical inspection devices 1 from FIGS. 1 and 2 are not restricted to the illustrated orientations of containers 2 but are configured for the inspection containers 2 with any random orientation relative to the device.

Furthermore, the optical inspection devices of FIGS. 1 and 2 also comprise an image processing device (presently not shown) in a computer, where the optical inspection method is stored as a computer program product (software) in a memory and executed on a microprocessor.

It is understood that the features mentioned in the embodiments described above are not restricted to these specific combinations and are also possible in any other combination.

What is claimed is:

1. An optical inspection method for containers, comprising:
    at least partly illuminating or transilluminating a container with light of an illuminating device and capturing from different viewing directions as a camera image in each case by means of at least one camera,
    ascertaining, in a first image analysis step, first image information of a first inspection zone of said container from at least two of said camera images by stereoscopically pairing image points, wherein said stereoscopically pairing comprises at least one of two-dimensional superpositioning of said camera images, perspective equalization of said camera images, associating 3D-points on the container with respective image points of said camera images, ascertaining a three-dimensional position of a feature on said container, and photogrammetric analysis of said camera images or triangulation analysis of said camera images, and
    analyzing in a second image analysis step, an individual camera image of said two camera images, wherein said first image information is first excluded and second image information of a second inspection zone (B) of said container is then ascertained.

2. The optical inspection method according to claim 1, wherein one of said camera images is analyzed in a third image analysis step, where said second image information is first excluded and then third image information of a third inspection zone (C) of said container is ascertained.

3. The optical inspection method according to claim 2, wherein said second inspection zone (B) is in the viewing direction (R5) of said camera image used in said second image analysis step arranged behind said first inspection zone (A), and said third inspection zone (C) is in the viewing direction (R4) of said camera image used in said third image analysis step arranged in front of said second inspection zone (B).

4. The optical inspection method according to claim 2, wherein in said third image analysis step, a different camera image is analyzed than in said second image analysis step.

5. The optical inspection method according to claim 2, wherein said third inspection zone (C) is captured only by said camera image analyzed in said third image analysis step.

6. The optical inspection method according to claim 1, wherein said inspection zones (A-C) do not overlap each other.

7. The optical inspection method according to claim 1, wherein said image information is ascertained by an imaging rule of said camera which correlates spatial points and image points with one another, for example, by way of lens parameters.

8. The optical inspection method according to claim 1, wherein said inspection zones (A-C) are each associated with different sections of said container.

9. An optical inspection device for containers with an illuminating device and at least one camera which is at least partly directed onto a light-emitting surface of said illuminating device, and with an image processing device, said image processing device configured to perform the optical inspection method according to claim 1.

10. The optical inspection device according to claim 9, wherein a mirror cabinet is arranged in front of said camera for capturing several viewing directions onto said container in one camera image.

11. A computer program product on a non-transitory computer readable data carrier comprising machine commands for a microprocessor for performing the optical inspection method according to claim 1.

* * * * *